United States Patent [19]

Anglin

[11] Patent Number: 5,413,916
[45] Date of Patent: May 9, 1995

[54] COLORIMETRIC TOXICITY TEST
[75] Inventor: Robert Anglin, Loveland, Colo.
[73] Assignee: Hach Company, Loveland, Colo.
[21] Appl. No.: 175,136
[22] Filed: Dec. 29, 1993
[51] Int. Cl.⁶ .................. C12Q 1/00; C12N 1/00
[52] U.S. Cl. .................................. 435/29; 435/4;
    435/968; 435/25; 435/26; 436/172; 436/800
[58] Field of Search ............... 435/4, 29, 968, 25,
    435/26; 436/172, 800

[56] References Cited

U.S. PATENT DOCUMENTS 3,957,580 5/1976 Nelson ..................... 435/181
5,045,477 9/1991 Belly et al. ................... 435/4

OTHER PUBLICATIONS

Liv, Bull. Environ. Contam. Toxicol. vol. 26 pp. 145–149 (1981).

Primary Examiner—David A. Redding
Assistant Examiner—Jane Williams
Attorney, Agent, or Firm—Dean P. Edmundson

[57] ABSTRACT

A method is described for determining the toxicity of an environmental sample to bacteria. The method includes the use of resazurin dye as an indicator. Glutaraldehyde is used as an accelerating agent to speed the test.

6 Claims, No Drawings

COLORIMETRIC TOXICITY TEST

FIELD OF THE INVENTION

This invention relates to toxicity testing. More particularly, this invention relates to toxicity testing using bacterial indicator organisms. Even more particularly, this invention relates to a toxicity test involving chemically-accelerated reduction of resazurin by bacterial respiration.

BACKGROUND OF THE INVENTION

Toxicity of chemicals to organisms is important in determining how chemicals in an environmental sample will behave in nature. Various types of tests have been used to determine the extent of toxicity of chemicals to microorganisms. Microbial toxicity tests are advantageous because of the short life cycles of the organisms and the high test concentrations which can be used.

Liu, "A Rapid Biochemical Test For Measuring Chemical Toxicity", Bull, Environm. Contam. Toxicol., 26, 14–149 (1981), incorporated herein by reference, describes a biochemical toxicity test based on reduction of resazurin by bacterial respiration. Resazurin is a redox-active dye which, when reduced, changes color from blue to pink. Substances which are toxic to bacteria can inhibit their metabolism and thus inhibit the rate of resazurin reduction. The method as described by Liu involved an organic solvent extraction and centrifugation. These steps are time consuming and cumbersome. Also, the extracting solvent used, n-amyl alcohol, has toxicity problems associated with it.

A commercially-available test known as "MicroTox" measures the effect of toxins on the light output of luminescent bacteria. Bioluminescence is not an essential metabolic process nor is it widespread among living organisms. Toxins that specifically inhibit luciferase may not exhibit general toxity to other organisms. In addition, measuring luminescence requires use of a very expensive instrument.

Another commercially-available test is known as "Toxi-Chromotest" which measures the cleavage of X-Gal or ONPG by the $\beta$-galactosidase enzyme of a strain of *Escherichia Coli* that is highly sensitive to toxins. What is actually measured in this test is the ability of the organism to synthesize the enzyme. The test is limited to the use of one genetically engineered strain of *E. coli*.

Another commercial test is known as the IQ Toxicity Test which measures the cleavage of a fluorescent dye by the $\beta$-glucuronidase enzyme of Daphnia (water fleas). In this case the activity of one enzyme is used to represent the viability of the organism.

The PolyTox test is also commercially available. It measures the reduction of oxygen consumption by bacteria. It requires the use of a dissolved oxygen electrode. Only one test can be run at a time. The information gained from this test is similar to that obtained from the resazurin reduction method but it requires more expensive equipment, and multiple tests require more time and sample manipulation.

The foregoing tests are all designated to be used with a specific organism. Users are not given the option of determining the toxicity of substances to their own biomass.

There has not heretofore been described a simple and rapid chemical toxicity test of the type described herein.

Respiration is the process that generates ATP (adenosine triphosphate) using the energy from the oxidation of an electron donor by an external electron acceptor. In the case of aerobic respiration the terminal electron acceptor is $O_2$. Electrons are transferred from the electron donor to the terminal electron acceptor through a series of electron-transfer proteins that are imbedded in the cell membrane. Some substances, such as redox-active dyes like resazurin, can act as alternative electron acceptors by oxidizing one of the membrane proteins.

Electron transfer is coupled to ATP generation by proton gradient across the cell membrane that is created as electrons flow through the membrane-bound electron transfer system. ATP is synthesized from ADP (adenosine diphosphate) and inorganic phosphate when this proton gradient is used to drive the phosphorylation of ADP by a membrane-spanning ATPase.

Since it involves the creation and maintenance of a proton gradient across the cell membrane, respiration is affected by substances that make the membrane permeable to protons. When protons can cross the membrane freely, bacteria can not use a proton gradient to make ATP. The oxidation of energy sources is thereby uncoupled from the phosphorylation of ADP. Substances that uncouple oxidation from phosphorylation in this way are often organic acids like phenols that are lipid soluble but can become protonated on the outside of the membrane, diffuse across the membrane and then become deprotonated on the inside of the membrane.

Since the rate of catabolic processes is controlled by the ADP/ATP ratio, these processes are accelerated by the uncoupling of oxidation from phosphorylation. Some substances that cannot act as proton shuttles uncouple oxidation from phosphorylation by inhibiting the ATPase that uses the proton gradient to synthesize ATP.

The result of the action of uncouplers in toxicity test is twofold. Reactions that are dependent upon the concentration of reduced coenzymes and ATP are slowed due to a decrease in the concentration of substrates. Reactions like the reduction of resazurin that are dependent upon the rate of electron transfer are accelerated.

SUMMARY OF THE INVENTION

In accordance with the present invention there is provided a method for accelerating the reaction rate of resazurin reduction in the toxicity test by means of the use of a membrane-active agent, i.e., glutaraldehyde. The use of glutaraldehyde to accelerate the reaction allows the use of a lower level of inoculum to reduce resazurin dye. Consequently, the absorbance of the dye can be read in a colorimeter without removing the bacterial cells from the light path. The color change of the dye is very dramatic and can easily be distinguished visually.

Thus, the toxicity test can be performed very rapidly as compared to prior tests. Also, the toxicity test enables the use of colorimetric techniques without filtering, extraction, or centrifugation. The toxicity test of this invention, unlike previous tests, can be used with many different species of bacteria.

DETAILED DESCRIPTION OF THE INVENTION

Glutaraldehyde is a linear, five-carbon molecule with two aldehyde groups. Each aldehyde group can react to form a Schiff base linkage with an amino group on a protein. It is commonly used as a bactericide. It is thought to act by forming crosslinks between membrane proteins. Glutaraldehyde is also used to immobilize cells and proteins on solid supports.

The mechanism by which glutaraldehyde accelerates the dye reduction in the test of this invention is not known. It has no easily ionizable chemical functional groups that would allow it to act as a proton shuttle like many known uncouplers. It also has no reversibly oxidizable groups which would allow it to shuttle electrons across the membrane like some other uncouplers. Some substances uncouple oxidation from phosphorylation by inhibiting the ATPase that uses the proton gradient to synthesize ATP from ADP. It is possible that glutaraldehyde acts in this way.

It has been found that glutaraldehyde inhibits oxygen consumption as measured with a dissolved oxygen electrode. It is possible that in addition to increasing membrane permeability, glutaraldehyde also interferes with electron transfer to $O_2$ by a different mechanism. The present invention takes advantage of the accelerating effect of glutaraldehyde on resazurin reduction to provide a more convenient assay for toxicity without compromising its effectiveness.

The resazurin reduction can be used with many different species of bacteria and perhaps with some eukaryotes. This allows the user to culture his or her own organisms and determine the toxicity of a waste stream to the bacteria that will be exposed to it. Glutaraldehyde has a similar effect on several species of bacteria, including both gram-positive and gram-negative species. It allows the resazurin reduction method to be run in a timely and convenient manner using inexpensive equipment.

The test procedure used for determining toxicity of an environmental sample (e.g., a water sample or other material) to bacteria involves:

1. Growing the desired bacteria to form an inoculum.
2. Adding the environmental test sample to a vial.
3. Adding resazurin dye and nutrients to the test sample vial.
4. Adding glutaraldehyde to the test sample vial and mixing the contents.
5. Adding a portion of the inoculum to the test sample vial.
6. Measuring light absorbance through the test sample vial using a spectrophotometer or a color comparator wheel. The change in light absorbance or color over time is compared to an appropriate blank, after which the % inhibition can be determined.

Most species of bacteria that grow in broth medium can be used as the inoculum for this test. The Total Bacteria Count medium available from Hach Company works well. It is a trypticase soy broth. All that is necessary is to inoculate the medium with bacteria and incubate until there is sufficient growth to make the culture tube opaque. Variations in the cell density and metabolic activity of the inocula are compensated for by running a negative control. These variations can cause variations in the amount of time required for the negative control to react completely. The amount of time required for the negative control to react is used to time the reaction of the sample. *Escherichia coli* Bactrol disks commercially available from Hach can also be used as a source of inoculum. Lauryl tryptose broth is the preferred growth medium for *E. coli*.

The % Inhibition results obtained do not necessarily increase in direct proportion to the concentration of toxins. In order to determine the minimum inhibitory concentration of toxin it is possible to make tenfold dilutions of the sample and determine the % Inhibition for the dilutions until the sample is diluted sufficiently so that no inhibition is observed.

EXAMPLE 1

Any conventional procedure is effective for inoculum development when using indigenous biomass. One simple procedure involves adding 1.0 mL of the source culture to a Total Bacterial Count vial and then incubating until the tube is visibly turbid. When using the Bactrol disk, the following procedure is preferably used.

1. Flame sterilize forceps by dipping in isopropanol and igniting with a flame. Allow to cool.
2. Remove the cap from the inoculum bottle and pick out a Bactrol inoculum disk with the sterilized forceps.
3. Remove the cap from a Lauryl Tryptose Broth Tube and drop in the inoculum disk. Shake to dissolve the disk.
4. Incubate until the broth medium is visibly turbid. Turbidity development will be much faster at 35° C. than at room temperature, and ten hours is normally sufficient.
5. Before using the developed source culture from step 4 to inoculate a toxicity test tube, inoculate a new Lauryl Tryptose Broth Tube by inverting the source culture vial and switching caps with an uninoculated vial and inverting the new vial. After incubation this new vial can be used in subsequent tests. In this way many medium vials can be inoculated from one Bactrol disk.

The procedure which is then used for measuring toxicity of a test sample in question may be either a spectrophotometric procedure or a color wheel procedure.

EXAMPLE 2

The spectrophotometric procedure involves:

1. Providing a suitable spectrophotomer such as the Hach DR/3000 set for operation in the absorbance mode.
2. For each sample to be tested, adding toxicity reagent to an empty reaction tube. A preferred toxicity reagent to be used comprises resazurin dye MOPS (4-morpholinepropanesulfonic acid), sodium MOPS, Difco nutrient broth, glucose and sodium acetate. Toxicity reagent is also added to another empty tube to be used as a negative control.
3. Adding 5 mL of deionized water to the negative control and 5 mL of test sample to each sample tube.
4. Adding 2 drops of glutaraldehyde solution (3.75% solution in water) to each tube, then capping each tube and inverting it to mix.
5. Adding 0.5 mL of the inoculum to each tube, then capping each tube and inverting it to mix.
6. Absorbance at 603 nm is measured for each tube versus a deionized water blank.
7. Allowing the solutions in the tubes to react until the absorbance of the negative control decreases to 0.60±0.10 (about 45–75 minutes).
8. Recording the absorbances of the tubes again versus a deionized water blank.
9. Calculating the % inhibition as follows:

$$\%\ I = [1 - (\Delta A_{sample}/\Delta A_{neg.\ control})] \times 100$$

Where $\Delta A = A_{initial} - A_{final}$

Some toxins accelerate respiration and will give a negative % Inhibition on all respiration-based toxicity tests. Samples which, upon repeated testing, consistently give less than $-10\%$ Inhibition on this test should be considered toxic.

EXAMPLE 3

The color wheel procedure involves:
1. Filling two color viewing tubes to the 5 mL mark for each sample to be tested. Two color viewing tubes are also filled to the 5 mL mark with deionized water for a negative control. In each case, one tube will serve as a color blank and one will be used for color development.
2. Adding toxicity reagent (as described above) to one of each pair of tubes from step 1. This tube will be the color development tube.
3. Adding 2 drops of glutaraldehyde solution (3.75% solution in water) to each tube, then capping each tube and inverting it to mix.
4. Adding 0.5 mL of the inoculum to each tube, then capping each tube and inverting it to mix.
5. Placing the color development tube and the color blank tube in a color comparator which is then held up to a light source. A color disk is rotated until the color matches the color in the window. Color wheel units can then be read in the scale window.
6. Allowing the solutions in the tubes to react until the color of the negative control approximately matches the color at "10" color wheel units (about 45–75 minutes). The reading for an exact color match is recorded.
7. Recording the color wheel units for the sample tube. The blue color is so intense that small differences are not visually distinguishable.

Other variants are possible without departing from the scope of this invention. For example, the amount of glutaraldehyde used may vary. Generally speaking, the reaction rate is increased with increasing amounts of glutaraldehyde added. A preferred concentration is 0.045% glutaraldehyde in the test sample, although concentrations as high as 1% and as low as 0.03% have been found to be useful. The methods of the invention can be used in testing toxicity of any type of environmental sample, e.g., liquid or solid. If excessive turbidity of the sample interferes with color viewing, the sample may be diluted as needed.

What is claimed is:

1. A method for determining the toxicity of an environmental sample to bacteria, the method comprising the steps of:
    (a) providing a bacterial culture;
    (b) adding resazurin to said sample;
    (c) adding glutaraldehyde to said sample;
    (d) adding a portion of said bacterial culture to said sample;
    (e) measuring light absorbance through the sample and comparing said absorbance to light absorbance through a blank.

2. A method in accordance with claim 1, wherein said bacterial culture comprises *E. coli*.

3. A method in accordance with claim 1, further comprising the step of adding nutrients to said sample.

4. A method in accordance with claim 1, wherein said light absorbance is measured by means of a spectrophotometer.

5. A method in accordance with claim 1, wherein said sample comprises a water sample.

6. In a method for determining the toxicity of an environmental sample to bacteria, wherein the method includes the steps of adding resazurin and a bacterial culture to the sample and then measuring light absorbance through the sample, wherein the improvement comprises the steps of:
    (a) adding glutaraldehyde to said sample, and
    (b) comparing light absorbance through the sample to light absorbance through a blank.

* * * * *